United States Patent [19]

Bingham

[11] 4,240,967
[45] Dec. 23, 1980

[54] ORGANIC PIGMENTS DERIVED FROM COUMARIN

[75] Inventor: Richard C. Bingham, Wilmington, Del.

[73] Assignee: E. I. Du Pont de Nemours and Company, Wilmington, Del.

[21] Appl. No.: 65,863

[22] Filed: Aug. 13, 1979

Related U.S. Application Data

[63] Continuation-in-part of Ser. No. 877,462, Feb. 13, 1978, abandoned.

[30] Foreign Application Priority Data

Feb. 9, 1979 [CA] Canada .................................. 321189
Feb. 9, 1979 [GB] United Kingdom ................. 4633/79

[51] Int. Cl.³ .......................................... C07D 311/08
[52] U.S. Cl. .................................. 260/343.45; 106/309
[58] Field of Search ................................... 260/343.45

[56] References Cited

U.S. PATENT DOCUMENTS 3,509,177  4/1970  McIntyre ........................ 260/343.45

FOREIGN PATENT DOCUMENTS 1470053  2/1967  France .

OTHER PUBLICATIONS

Bassignana et al. Tetrahedron, vol. 20, 1964, pp. 2859–2871.

Primary Examiner—John D. Randolph
Assistant Examiner—Jane T. Fan

[57] ABSTRACT

This application is directed to compounds which are useful as pigments. The compounds are represented by the formula:

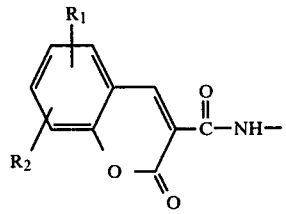

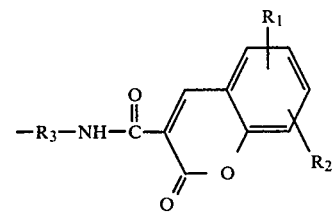

where
$R_1$ is hydrogen, alkyl of 1 to 4 carbon atoms, alkoxy of 1 to 4 carbon atoms, chlorine or bromine;
$R_2$ is hydrogen, alkyl of 1 to 4 carbon atoms, alkoxy of 1 to 4 carbon atoms, chlorine, bromine and nitro; and

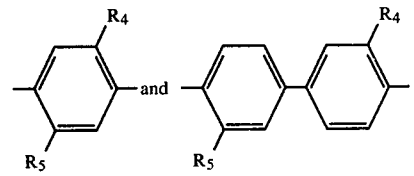

where $R_4$ and $R_5$ are hydrogen, alkyl of 1 to 4 carbon atoms, alkoxy of 1 to 4 carbon atoms, chlorine or bromine.

8 Claims, No Drawings

ORGANIC PIGMENTS DERIVED FROM COUMARIN

CROSS-REFERENCE TO RELATED APPLICATION

This application is a continuation-in-part of application Ser. No. 877,462, filed Feb. 13, 1978 now abandoned.

BACKGROUND OF THE INVENTION

This invention relates to derivatives of coumarin compounds, useful as pigments, which are primrose yellow to orange in color.

Heavy metal yellow pigments such as lead chromate, cadmium sulfide, and nickel titanate have been widely used in the paint and plastics industry for many years. However, the potential toxicity and environmental problems associated with their production and use has recently caused industry to search for alternatives to these heavy metal pigments.

Organic yellow pigments free from heavy metals provide a possible alternative to the inorganic yellows currently in use. Such alternatives must, however, offer excellent bleedfastness and durability. They also must offer bright intense shades so that they may be extended with a white pigment, such as $TiO_2$, to obtain needed opacity while retaining the needed color strength. The available organic yellow pigments do not satisfy all of these requirements.

There are six basic types of organic yellow pigments currently in use (Reference: J. Lenoir in "The Chemistry of Synthetic Dyes", Vol. V, K. Venkataramen, Ed., Academic Press, New York, 1971). These are mono azo diarylide, condensation azo, isoindolinone, anthraquinone, and metal chelate pigments. Each group suffers from one or more disadvantages. Mono azo yellows generally have poor bleedfastness and marginal durability. Diarylide yellows have poor durability and their production requires the use of benzidenes which are suspected carcinogens. Condensation azo yellows have marginal durability and are expensive to use. Isoindolinone and anthraquinone yellows have relatively low color strength and are expensive to use. Metal chelate yellows are dull, often green pigments which do not completely avoid the heavy metal problem.

The present invention relates to a new class of yellow to orange organic pigments. These new compounds provide bright intense colors which exhibit excellent bleedfastness and durability. They are particularly useful in the pigmentation of paints, plastics, and inks.

SUMMARY OF THE INVENTION

This invention relates to compounds of the formula:

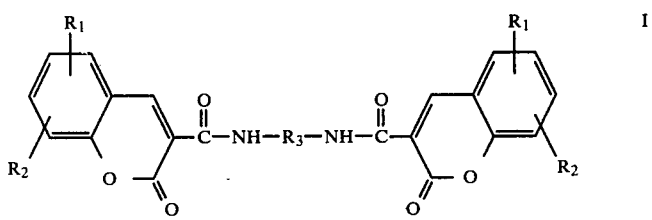

where
$R_1$ is hydrogen, alkyl of 1 to 4 carbon atoms, alkoxy of 1 to 4 carbon atoms, chlorine or bromine;
$R_2$ is hydrogen, alkyl of 1 to 4 carbon atoms, alkoxy of 1 to 4 carbon atoms, chlorine, bromine and nitro; and
$R_3$ is

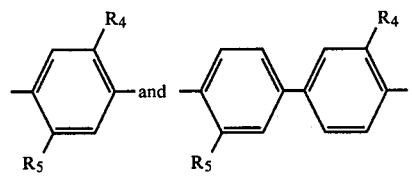

where $R_4$ and $R_5$ are hydrogen, alkyl of 1 to 4 carbon atoms, alkoxy of 1 to 4 carbon atoms, chlorine or bromine.

DETAILED DESCRIPTION OF THE INVENTION

As stated above the present invention relates to a new class of organic pigments which vary in color from yellow to orange. These new compounds provide bright, intense colors which exhibit excellent bleedfastness and durability and are characterized by Formula I. The compounds of this invention are derived from coumarin and an aromatic diamine. It will be understood that the compounds derived from coumarin and a phenyl or substituted phenyl diamine are represented by the formula:

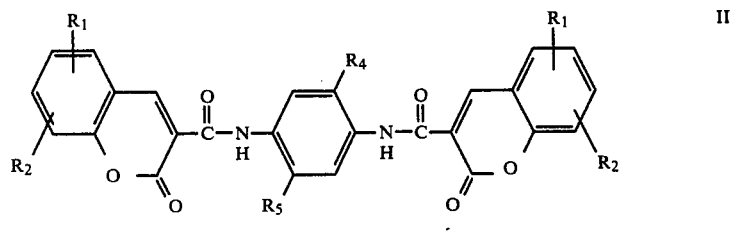

wherein
$R_1$ is hydrogen, alkyl of 1 to 4 carbon atoms, alkoxy of 1 to 4 carbon atoms, chlorine and bromine;
$R_2$ is hydrogen, alkyl of 1 to 4 carbon atoms, alkoxy of 1 to 4 carbon atoms, chlorine, bromine and nitro; and
$R_4$ and $R_5$ are each hydrogen, alkyl of 1 to 4 carbon atoms, alkoxy of 1 to 4 carbon atoms, chloro and bromo.

It will be understood that the cmpounds derived from coumarin and biphenyl or substituted biphenyl diamine are represented by the formula:

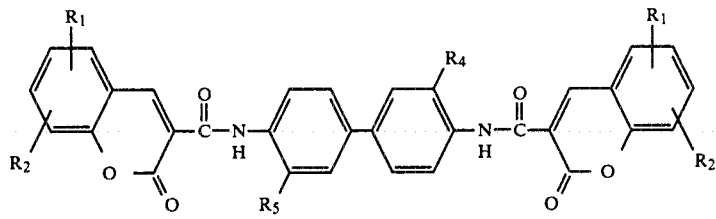

wherein $R_1$ is hydrogen, alkyl of 1 to 4 carbon atoms alkoxy of 1 to 4 carbon atoms, chlorine and bromine;

$R_2$ is hydrogen, alkyl of 1 to 4 carbon atoms, alkoxy of 1 to 4 carbon atoms, chlorine, bromine and nitro; and $R_4$ and $R_5$ are each hydrogen, alkyl of 1 to 4 carbon atoms, alkoxy of 1 to 4 carbon atoms, chlorine and bromine.

It will be understood that those compounds of Formula I are preferred in which $R_1$, $R_2$, $R_4$ and $R_5$ are hydrogen chlorine, methyl or methoxy.

Most preferred compounds of this invention are those compounds of Formula II in which $R_1$, $R_2$ and $R_4$ are hydrogen or chlorine and $R_5$ is hydrogen.

The compounds of this invention vary in color from greenish yellow to reddish yellow shade range. For example when $R_1$-$R_4$ are hydrogen the compound is a bright medium shade yellow, but when $R_1$ or $R_2$ are halogen or nitro and $R_4$ or $R_5$ is an alkyl or alkoxy, the compound is of a reddish hue. Therefore, by varying the various substituents on the compounds backbone, one can obtain numerous shades of yellow to orange pigment.

The color of the compounds of this invention would not be predicted by the solution spectra techniques commonly used in pigments research, and although not fully understood the color of the compounds of this invention are believed to be the result of unique intermolecular interactions in the solid state.

It should also be understood that the compounds of this invention have very low solubility in organic solvents and show excellent bleed resistance in typical alkyd or lacquer paints as determined by an overstripe bleed test. In addition the compounds of this invention also exhibit excellent resistance to migration in plastics such as polyvinyl chloride.

The compounds of this invention also demonstrate acceptable lightfastness when dispersed in a typical paint or plastic dispersion and exposed in a fadometer. The compounds of this invention also possess sufficient heat stability to be dispersed into molten plastics such as polystyrene.

The compounds of this invention can be prepared by various methods. The preferred method for preparing the compounds of this invention involves heating an appropriate coumarin carbonyl chloride with an appropriate aromatic diamine in the presence of a suitable solvent such as o-dichlorobenzene, toluene, or Dowtherm ® A (an eutectic mixture consisting of 23.5 weight percent biphenyl and 76.5 weight percent of diphenyl oxide).

An alternative method for preparing the compounds of this invention involves heating a carboxylic acid ester of an appropriate coumarin with an appropriate aromatic diamine in the presence of sodium carbonate and suitable solvent.

EXAMPLE 1

A mixture of 10 g of a coumarin-3-carbonyl chloride, 2.6 g of p-phenylenediamine and 250 ml of o-dichlorobenzene is heated at 140°–150° C. for six hours. The product precipitates and is collected by filtration of the hot reaction mixture. It is washed with methanol and dried. The yield is 10.3 g (96% of theoretical) of bright yellow N,N'-p-phenylene bis(2-oxo-2H-1-benzopyran-3-carboxamide), which does not melt below 350° C.

Anal. calculated for $C_{26}H_{16}N_2O_6$; C, 69.2; H, 3.6; N, 6.2. Found: C, 69.0; H, 3.8; N, 6.4.

EXAMPLE 2

A mixture of 21.8 g of ethyl coumarin-3-carboxylate, 5.4 g of p-phenylenediamine and 5.3 g of sodium carbonate in 200 ml of Dowtherm ® A (an eutectic mixture of 23.5% of diphenyl and 76.5% of diphenyl oxide) is heated at 200°±5° C. for six hours. A steam jacketed condenser is used to facilitate ethanol removal from the reaction mixture. The product precipitates and is collected by filtration of the hot reaction mixture. The product is washed with methanol, water and dimethylformamide. After drying, the yield is 21.5 g (95% of theoretical) of N,N'-p-phenylene bis(2-oxo-2H-1-benzopyran-3-carboxamide).

Similar results are obtained if, for example, potassium acetate or sodium ethoxide is used in place of sodium carbonate.

EXAMPLE 3

A mixture of 12.2 g of salicylaldehyde, 16.0 g of ethyl malonate and 9.8 g of potassium acetate in 200 ml of Dowtherm ® A is heated at 175° C. for six hours. A steam jacketed condenser and a moderate vacuum (approximately 40 mm of mercury) are used to facilitate water and ethanol removal from the reaction mixture.

The reaction mixture is cooled to room temperature and 5.4 g of p-phenylenediamine is added. The reaction is then reheated to 200°±10° C. for six hours. After cooling to 100° C., the precipitated product is collected by filtration, washed with methanol and water and dried. The yield is 15.4 g (68.5% of theoretical) of N,N'-p-phenylene bis(2-oxo-2H-1-benzopyran-3-carboxamide).

EXAMPLE 4

A mixture of 35 g of coumarin-3-carbonyl chloride, 12 g of 2-chloro-p-phenylenediamine and 1 liter of Dowtherm ® A is heated at 100° C. for six hours under a vacuum of of approximately 60 MM of mercury. The product is collected by filtration of the hot reaction mixture. It is washed thoroughly with methanol and dried. The yield is 38.3 g of yellow N,N'-(2'-chloro- 1',4'-phenylene)bis(2-oxo-2H-1-benzopyran-3-carboxamide).

Anal. calc'd. for $C_{26}H_{15}N_2O_6Cl$: C, 64.14; H, 3.11; N, 5.75; Cl, 7.28. Found: C, 64.45; H, 3.30; N, 5.61; Cl, 7.22.

The product was dispersed in thermoplastic acrylic lacquer paint by ball milling. A portion of this paint was extended with sufficient titanium dioxide pigment to give a final toner to white ratio of 5/95. Another portion of the paint was extended with sufficient aluminum flake to give a toner to metal ratio of 90/10. The three paints were sprayed on primer coated aluminum panels. The durability of the paints was determined by placing the panels outdoors in a southern exposure. After six months, the durability of the paints was superior to those prepared in a similar manner from Irgazin ® Yellow 2GLT, a commercial yellow pigment similar in hue to the product of Example 4.

The bleedfastness of the product of this example in the thermoplastic acrylic lacquer paint is determined by spraying the masstone color on a primer coated aluminum panel and then spraying a white overstripe lacquer film. The panel is baked in an oven at 150° C. for 30 minutes. No migration of the yellow pigment into the white overstripe can be detected.

EXAMPLE 4A

A mixture of 12.2 g of salicylaldehyde, 16.0 g of ethyl malonate and 5.3 g of anhydrous sodium carbonate in 250 ml of Dowtherm ® A is heated at 150° C. under a moderate vacuum (approximately 60 MM) for four hours. The vacuum is then removed and 7.1 g of 2-chloro-p-phenylenediamine slurried in 50 ml of Dowtherm ® A is added in one portion. The reaction temperature is raised to 210° C. and held for two hours. The reaction mixture is then cooled to 100° C. and filtered. The product is washed with methanol and water. After drying the yield is 19.6 g of greenish-yellow N,N'-(2'-chloro-1',4'-phenylene)bis(2-oxo-2H-1-benzopyran-3-carboxamide).

The material prepared in this manner is a structurally isomeric form of the product described in Example 4. Although both materials have the same chemical composition, they show different X-ray spectra.

The material prepared by the Example may be converted to the more desirable form obtained in Example 4 by a variety of techniques which are standard to pigment technology such as acid pasting, or solvent milling.

EXAMPLE 5

A mixture of 10 g of 6-nitrocoumarin-3-carbonyl chloride, 2.1 g of p-phenylenediamine and 250 ml of o-dihclorobenzene is heated at 150°±5° C. for six hours. The product is collected by filtration, washed with methanol and dried. The yield is 7.6 g of bright yellow N,N'-p-phenylene bis(2-oxo-6-nitro-2H-1-benzopyran-3-carboxamide).

Anal. calc'd. for $C_{26}H_{14}N_4O_{10}$: C, 57.57; H, 2.60; N, 10.33. Found: C, 57.30; H, 2.81; N, 9.98.

EXAMPLES 6–33

Additional compounds of Formulas II or III listed in Table I may be prepared according to the procedure described in Example 1 by heating Reactant 1 with Reactant 2 to obtain the indicated product.

TABLE I

| Example No. | Reactant 1 | Reactant 2 | Product |
|---|---|---|---|
| 6 | (coumarin-3-COCl) | 2,5-dichloro-1,4-phenylenediamine (Cl, Cl, H₂N, NH₂) | N,N'-(2',5'-dichloro-1',4'-phenylene)bis(2-oxo-2H-1-benzopyran-3-carboxamide) |
| 7 | " | 2-chloro-5-methyl-1,4-phenylenediamine (Cl, CH₃, H₂N, NH₂) | N,N'-(2'-chloro-5'-methyl-1',4'-phenylene)bis(2-oxo-2H-1-benzopyran-3-carboxamide) |
| 8 | " | 2-chloro-5-methoxy-1,4-phenylenediamine (Cl, OCH₃, H₂N, NH₂) | N,N'-(2'-chloro-5'-methoxy-1',4'-phenylene)bis(2-oxo-2H-1-benzopyran-3-carboxamide) |
| 9 | " | 2-methoxy-1,4-phenylenediamine (OCH₃, H₂N, NH₂) | N,N'-(2'-methoxy-1',4'-phenylene)bis(2-oxo-2H-1-benzopyran-3-carboxamide) |
| 10 | " | 2,5-dimethoxy-1,4-phenylenediamine (OCH₃, OCH₃, H₂N, NH₂) | N,N'-(2',5'-dimethoxy-1',4'-phenylene)bis(2-oxo-2H-1-benzopyran-3-carboxamide) |
| 11 | " | 2-methyl-1,4-phenylenediamine (CH₃, H₂N, NH₂) | N,N'-(2'-methyl-1',4'-phenylene)bis(2-oxo-2H-1-benzopyran-3-carboxamide) |
| 12 | " | 2,5-dimethyl-1,4-phenylenediamine (CH₃, CH₃, H₂N, NH₂) | N,N'-(2',5'-dimethyl-1',4'-phenylene)bis(2-oxo-2H-1-benzopyran-3-carboxamide) |

TABLE I-continued

| Example No. | Reactant 1 | Reactant 2 | Product |
|---|---|---|---|
| 13 | " | 4-bromo-1,3-phenylenediamine (H₂N–C₆H₃(Br)–NH₂) | N,N'-(2'-bromo-1',4'-phenylene)bis(2-oxo-2H-1-benzopyran-3-carboxamide) |
| 14 | " | 2,5-dibromo-1,4-phenylenediamine | N,N'-(2',5'-dibromo-1',4'-phenylene)bis(2-oxo-2H-1-benzopyran-3-carboxamide) |
| 15 | " | 2-bromo-5-methyl-1,4-phenylenediamine | N,N'-(2'-bromo,5'-methyl-1',4'-phenylene)bis-(2-oxo-2H-1-benzopyran-3-carboxamide) |
| 16 | 6,8-dichloro-2-oxo-2H-1-benzopyran-3-carbonyl chloride | p-phenylenediamine | N,N'-p-phenylene bis(2-oxo-6,8-dichloro-2H-1-benzopyran--3-carboxamide) |
| 17 | " | 2-chloro-1,4-phenylenediamine | N,N'-(2-chloro-1',4'-phenylene)-bis(2-oxo-6,8-dichloro-2H-1-benzopyran-3-carboxamide) |
| 18 | " | 2,5-dichloro-1,4-phenylenediamine | N,N'-(2',5'-dichloro-1',4'-phenylene)bis(2-oxo-6,8-dichloro-2H-1-benzopyran-3-carboxamide) |
| 19 | " | 2-methoxy-1,4-phenylenediamine | N,N'-(2'-methoxy-1',4'-phenylene)bis(2-oxo-6,8-dichloro-2H-1-benzopyran-3-carboxamide) |
| 20 | " | 2-methyl-1,4-phenylenediamine | N,N'-(2'-methyl-1',4'-phenylene)bis(2-oxo-6,8-dichloro-2H-1-benzopyran-3-carboxamide) |
| 21 | " | 2-methoxy-5-methyl-1,4-phenylenediamine | N,N'-(2'-methoxy-5'-methyl-1',4'-phenylene)bis(2-oxo-6,8-dichloro-2H-1-benzopyran-3-carboxamide) |
| 22 | " | 2-chloro-5-methyl-1,4-phenylenediamine | N,N'-(2'-chloro-5'-methyl-1',4'-phenylene)bis(2-oxo-6,8-dichloro-2H-1-benzopyran-3-carboxamide) |
| 23 | 6-chloro-2-oxo-2H-1-benzopyran-3-carbonyl chloride | p-phenylenediamine | N,N'-1',4'-phenylene bis(2-oxo--6-chloro-2H-1-benzopyran-3-carboxamide) |
| 24 | " | 2-chloro-1,4-phenylenediamine | N,N'-(2'-chloro-1',4'-phenylene)-bis(2-oxo-6-chloro-2H-1-benzopyran-3-carboxamide) |
| 25 | " | 2-methyl-1,4-phenylenediamine | N,N'-(2'-methyl-1',4'-phenylene)-bis(2-oxo-6-chloro-2H-1-benzopyran-3-carboxamide) |
| 26 | " | 2,5-dichloro-1,4-phenylenediamine | N,N'-(2',5'-dichloro-1',4'-phenylene)bis(2-oxo-6-chloro-2H-1-benzopyran-3-carboxamide) |
| 27 | 6-methoxy-2-oxo-2H-1-benzopyran-3-carbonyl chloride | p-phenylenediamine | N,N'-p-phenylene bis(2-oxo-6-methoxy-2H-1-benzopyran-3-carboxamide) |
| 28 | 6-bromo-2-oxo-2H-1-benzopyran-3-carbonyl chloride | p-phenylenediamine | N,N'-p-phenylene bis(2-oxo-6-bromo-2H-1-benzopyran-3-carboxamide) |

TABLE I-continued

| Example No. | Reactant 1 | Reactant 2 | Product |
|---|---|---|---|
| 29 | CH₃-benzopyran-COCl | H₂N—⟨phenyl⟩—NH₂ | N,N'-p-phenylene bis(2-oxo-6-methyl-2H-1-benzopyran-3-carboxamide) |
| 30 | 8-NO₂-benzopyran-COCl | H₂N—⟨phenyl⟩—NH₂ | N,N'-p-phenylene bis(2-oxo-8-nitro-2H-1-benzopyran-3-carboxamide) |
| 31 | benzopyran-COCl | H₂N—⟨biphenyl⟩—NH₂ | N,N'-4,4'-biphenylene bis(2-oxo-2H-1-benzopyran-3-carboxamide) |
| 32 | benzopyran-COCl | H₂N—⟨3,3'-dichlorobiphenyl⟩—NH₂ | N,N'-(3,3'-dichloro-4,4'-biphenylene) bis(2-oxo-2H-1-benzopyran-3-carboxamide) |
| 33 | benzopyran-COCl | H₂N—⟨3,3'-dimethoxybiphenyl⟩—NH₂ | N,N'-(3,3'-dimethoxy-4,4'-biphenylene) bis(2-oxo-2H-1-benzopyran-3-carboxamide) |

What is claimed is:

1. A compound of the formula:

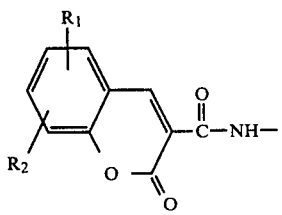

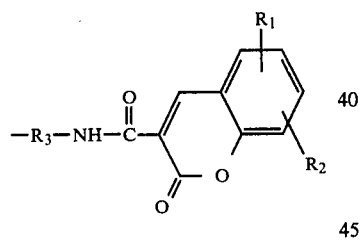

where
$R_1$ is hydrogen, alkyl of 1 to 4 carbon atoms, alkoxy of 1 to 4 carbon atoms, chlorine or bromine;
$R_2$ is hydrogen, alkyl of 1 to 4 carbon atoms, alkoxy of 1 to 4 carbon atoms, chlorine, bromine or nitro; and
$R_3$ is

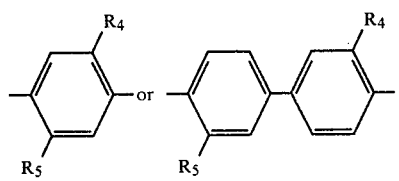

where $R_4$ and $R_5$ may be the same or different and are each hydrogen, alkyl of 1 to 4 carbon atoms, alkoxy of 1 to 4 carbon atoms, chlorine or bromine.

2. A compound of claim 1 in which $R_1$, $R_2$, $R_4$ and $R_5$ are selected from the group consisting of hydrogen, chlorine, methyl and methoxy.

3. A compound of claim 1 in which $R_3$ is

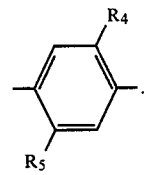

4. A compound of claim 2 in which $R_3$ is

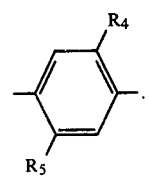

5. A compound of claim 1 in which $R_3$ is

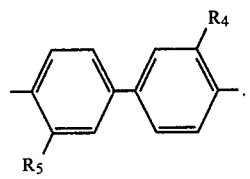

6. A compound of claim 2 in which $R_3$ is

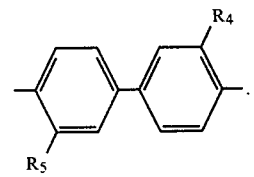

7. A compound of the formula:

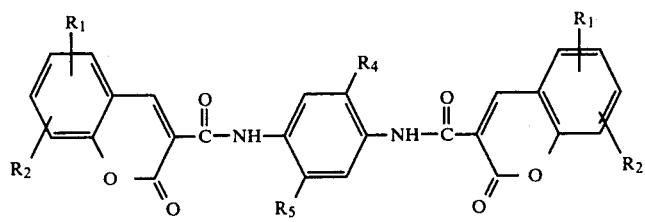
where
R₁ is hydrogen or chlorine,
R₂ is hydrogen or chlorine,
R₄ is hydrogen or chlorine, and
R₅ is hydrogen.
8. The compound N,N'-(2'-chloro-1',4'-phenylene)-bis(2-oxo-2H-1-benzopyran-3-carboxamide).
* * * * *